United States Patent [19]

Fry

[11] Patent Number: 4,807,633
[45] Date of Patent: Feb. 28, 1989

[54] NON-INVASIVE TISSUE THERMOMETRY SYSTEM AND METHOD

[75] Inventor: Francis J. Fry, Indianapolis, Ind.

[73] Assignee: Indianapolis Center for Advanced Research, Indianapolis, Ind.

[21] Appl. No.: 865,399

[22] Filed: May 21, 1986

[51] Int. Cl.$^4$ .............................................. A61B 10/00
[52] U.S. Cl. ............................... 128/660.02; 128/736; 73/599; 374/117
[58] Field of Search ...................... 128/660, 24 A, 804, 128/736; 73/597, 599, 602; 374/117, 119, 159

[56] References Cited

U.S. PATENT DOCUMENTS

| | | | |
|---|---|---|---|
| 3,233,450 | 2/1966 | Fry .................................. | 128/660 X |
| 3,738,171 | 6/1973 | Shepard et al. ...................... | 374/119 |
| 3,771,355 | 11/1973 | Sachs ...................................... | 73/597 |
| 4,246,784 | 1/1981 | Bowen .................................. | 374/117 |
| 4,399,441 | 8/1983 | Vaughan et al. ................ | 128/736 X |
| 4,452,081 | 6/1984 | Seppi ................................ | 374/119 X |
| 4,513,749 | 4/1985 | Kino et al. ...................... | 374/119 X |
| 4,513,750 | 4/1985 | Heyman et al. ................. | 374/117 X |
| 4,566,460 | 1/1986 | Sato et al. ........................ | 374/117 X |
| 4,607,341 | 8/1986 | Monchalin .......................... | 73/599 x |

OTHER PUBLICATIONS

Mobsby, E. G., "Practical Ultrasonic Thermometers", Ultrasonics Jan. 1969 pp. 39–42.
Ophic, J. et al, "Attenuation Estimation in Reflection, Progress and Prospects", Ultrasonic Imaging vol. 6 pp. 349–395 (1984).
Sachs, T. D. et al "TAST: A Non-Invasive Tissue Analytic System", NBS Spec. Publ. No. 453, Proc. of Seminar on Uts Tissue Characterization held at NBS, Gaithersburg, MD May 28–30, 1975 (Issued 10/76) pp. 153–163.

Primary Examiner—Francis J. Jaworski
Attorney, Agent, or Firm—Barnes & Thornburg

[57] ABSTRACT

It has been observed that attenuation of a transmitted or reflected beam of ultrasound in tissue irradiated with such a beam having a power intensity in the tissue in the non-linear range will change measurably as the tissue temperature changes. Based upon this observation, a method and apparatus for non-invasive thermometry include periodically interrogating the tissue with an ultrasonic beam having a power intensity sufficient such that the power intensity of the beam in the tissue is in the non-linear range. Attenuation coefficients based upon the attenuation of the power intensity of the ultrasonic beam due to the tissue are then periodically determined. Temperature changes in the tissue are determined based upon differences between the determined attenuation coefficients.

8 Claims, 2 Drawing Sheets

NON-INVASIVE TISSUE THERMOMETRY SYSTEM AND METHOD

This invention relates to a method and apparatus for non-invasively measuring temperature changes in tissue and more particularly, to a thermometry system and method which utilizes an ultrasound interrogating beam to determine temperature rise in tissue.

Treatment of cancer by hyperthermia is becoming an accepted manner of treatment. An ultrasound beam can be used to elevate the temperature of a malignant tumor in order to destroy it. For this treatment to be effective, the temperature of the tumor must be raised by something on the order of six to eight degrees Centigrade. By selecting the appropriate frequency of the ultrasonic beam to irradiate tissue containing the tumor, and by appropriate beam forming and/or sweeping, the temperature of the tissue at any given depth can be caused to rise without causing a significant increase in temperature in the surrounding tissue.

In order to utilize hyperthermic treatment effectively, the temperature of the tissue being heated must be carefully and accurately controlled. In existing hyperthermic treatment systems, thermocouples or other temperature sensors are actually implanted in the tissue which is to be heated. The outputs of these temperature sensors provide a temperature profile of the tissue being heated. This profile is used to control the power intensity of the ultrasonic beam heating the tissue in order to control the temperature of the heated tissue carefully.

A major disadvantage of this invasive technique of thermometry is that the thermocouples must be implanted in the body. The risk of infection or other complications always exists when invasive procedures must be performed in treatment. Additionally, hyperthermia cannot practically be used to treat cancerous tissue by techniques requiring invasive thermometry in some instances due to tumor location. The trauma which can accompany invasive thermometry creates a significant impediment to the use of ultrasound hyperthermia treatment.

Tissue which is irradiated by an ultrasonic beam has what is known as an ultrasonic attenuation coefficient. The attenuation coefficient is indicative of the power intensity loss of the ultrasonic beam due to its passage through the tissue. The attenuation coefficient thus reflects the difference between the power intensity of the ultrasonic beam at the point at which it enters the body being treated and the power intensity of the ultrasonic beam at any point inside the body, including the point at which it leaves the body being treated. One contributing factor to the attenuation coefficient is the power absorbed by the tissue being irradiated.

Non-invasive thermometry techniques are known. However, these known techniques utilize ultrasonic beams having spatial peak, temporal peak (SPTP) intensities sufficient to produce SPTP intensities on the order of 1 W/cm$^2$ in the tissue being measured. It has been observed in the laboratory that tissue exhibits a very minimal change in its attenuation coefficient for ultrasonic beams having power intensities on the order of 1 W/cm$^2$. Consequently, the attenuation coefficient of the beam is essentially constant for non-invasive thermometry schemes utilizing such low SPTP beams. This makes such thermometry methods difficult to use to measure temperatures accurately in the human clinical setting. For non-invasive human clinical thermometry, what are needed are SPTP powers in the so-called "high intensity-" or "non-linear-" or "finite amplitude-" range. This range includes SPTP powers on the order of, for example, 100 W/Cm$^2$ to 300 W/cm$^2$. In this finite amplitude range, temperature coefficients of ultrasound absorption and additional losses change by significant, readily detectable amounts, so that the received beam data can be compared against these changing coefficients to recover the temperature information by comparing the transmitted beam and the received beam. The spatial peak temporal average (SPTA) of the thermometry interrogating beam operating in pulse mode is to be maintained in the low milliwatt range so that this beam does not itself introduce a significant temperature rise.

It is an object of this invention to provide a non-invasive tissue thermometry system and method which has practical utility in the human clinical setting.

It is further an object of this invention to utilize an ultrasound interrogating beam to determine temperature rise in tissue accurately enough to control hyperthermic treatment means to achieve controlled therapeutic results.

The method of this invention for non-invasive thermometry in tissue comprises the step of periodically interrogating the tissue with an ultrasound beam having sufficient power intensity that the power intensity of the beam in the tissue is in the non-linear range. The method further comprises the step of periodically determining attenuation coefficients. The method further comprises the step of determining temperature changes in the tissue based upon differences between the determined attenuation coefficients.

A table of attenuation coefficients can be determined empirically by comparing the power intensity of the ultrasonic beam at the point it is generated, or enters a tissue sample, with the power intensity of the ultrasonic beam as it leaves a tissue sample, and measuring invasively the temperature of the tissue sample.

The system of the present invention comprises means for periodically interrogating tissue with an ultrasound beam having sufficient power intensity to create in the tissue a beam power intensity in the non-linear range. The apparatus further comprises means for periodically determining tissue attenuation coefficients. Temperature changes in the tissue are then determined based upon differences between determined attenuation coefficients.

This invention relates to applicant's discovery that the attenuation coefficient for tissue being irradiated with an ultrasonic beam having a power intensity level in the non-linear range in the tissue being irradiated changes in a readily detectable manner as the temperature of the tissue changes. This characteristic has heretofore not been appreciated by those skilled in the art to which this invention pertains.

The invention may better be understood by referring to the following detailed description of an embodiment of the invention. The detailed description particularly refers to the accompanying drawings in which.

An apparatus and method for non-invasively measuring temperature changes in tissue utilize an ultrasound interrogating beam to determine the temperature rise in tissue being heated. The interrogating beam must be operated in the finite amplitude range where the temperature coefficient of ultrasound absorption and related additional attenuation losses are sufficiently large to permit construction of practical devices useful for human clinical purposes. Applicant has discovered that operating the interrogating beam such that it has a power intensity level in the non-linear range in the tissue being heated causes the attenuation coefficient of the tissue to exhibit measurable changes as the temperature of the tissue changes. The attenuation coefficient is defined as the difference between the power intensity level of the ultrasound interrogating beam at its point of origination and the power intensity level of the ultrasound beam at a point where it leaves the tissue. It should be understood that the attenuation coefficient could also be determined by the difference between the power intensity level of the ultrasound interrogating beam at the point at which it enters the tissue and the point at which it leaves the tissue. Additionally, although the invention is described in the context of devices useful for human clinical purposes, this is illustrative only and is not meant to limit the scope of the invention.

Figure 1:
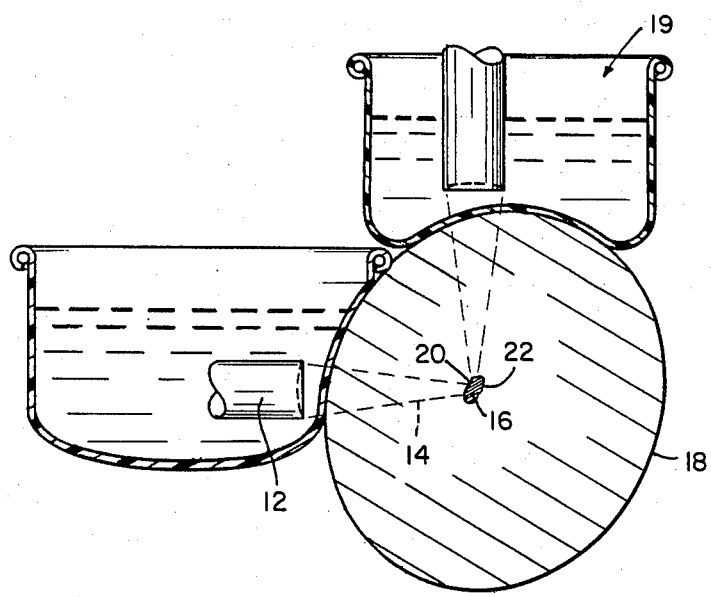
FIG. 1 is a diagramatic illustration of an apparatus according to the present invention.

Referring to FIG. 1, a non-invasive thermometry system 10 includes a means 12, such as an ultrasound transducer, for producing an ultrasound beam 14 for irradiating a target 16 such as a malignant tumor beneath the skin 18 of a patient. The power intensity of beam 14 is such that beam 14 will have a spatial peak, temporal peak (SPTP) intensity in the non-linear range, illustratively 200 W/cm$^2$, within target 16. Target 16 is illustratively a tissue mass within the body of a human patient undergoing hyperthermic treatment, such as by irradiation by an ultrasound transducer 19 operating in the linear range, illustratively at 1–10 W/cm$^2$ at target 16, and wherein target 16 is at some depth beneath skin 18. Ultrasonic beam 14 is reflected by the target 16 at points 20, 22 by scattering and/or specular reflection. The temperature in the tissue of target 16 is initially $T_n$ (normal body temperature). For this temperature, an attenuation coefficient (with components due to absorption, scattering, etc.) can be derived for the region between points 20, 22 of target 16. If the temperature in target 16 changes by $\Delta T$ to $T_n + \Delta T$, the change in the attenuation coefficient due to the change in temperature of the target 16 can be ascertained and the change in temperature of the target 16 can be found.

The magnitude of the absorption coefficient change for sound in the non-linear intensity range of 150 to 500 W/cm$^2$ SPTP is approximately 10 times as great as for sound intensities in the linear intensity range, typically below 10 W/cm$^2$ SPTP. This makes it much easier to use the ultrasound beam intensities in the non-linear range to determine temperature changes to the degree of accuracy required for human clinical hyperthermia treatment.

Referring to FIG. 1, a change in the pressure absorption coefficient alpha ($\alpha$) was experimentally determined. Letting the distance from point 20 to point 22 of target 16 be one centimeter and $\Delta T$ be 1° C., the change in the pressure absorption coefficient alpha for a 200 W/cm$^2$ sensing beam is approximately 4.6% per degree C. For liver tissue, the change in alpha was measured empirically by directly measuring alpha, irradiating the target 16, and measuring the temperature of the tissue. Table 1 contains the results of the measurements.

TABLE 1

| |
|---|
| $\alpha_{36° C.} = 0.0315$ |
| $\alpha_{37° C.} = 0.030$ |
| $\alpha_{38° C.} = 0.0285$ |

For a pulse-echo interrogation, wherein the power intensity level of the ultrasonic beam after it leaves the tissue is measured by a transducer placed at the point at which the beam is generated, the path length for the above example is 2 cm. The sound pressure amplitude (P) can be defined as $$P_{out} = P_{in} e^{-2\alpha}$$

where
P = pressure
$\alpha$ = pressure absorption coefficient in cm$^{-1}$.
2 = tissue path length in cm.

For 37° C., $P_{out37} = P_{in} e^{-0.030(2)}$

For 38° C., $P_{out38} = P_{in} e^{-0.0285(2)}$ $P_{out38} / P_{out37} = e^{0.003} = 1.003$ Therefore, it can be seen that as the temperature of the tissue being heated rises, the amount of sound which is absorbed by the tissue decreases which increases the power intensity level of the ultrasonic beam leaving the tissue.

Figure 2:
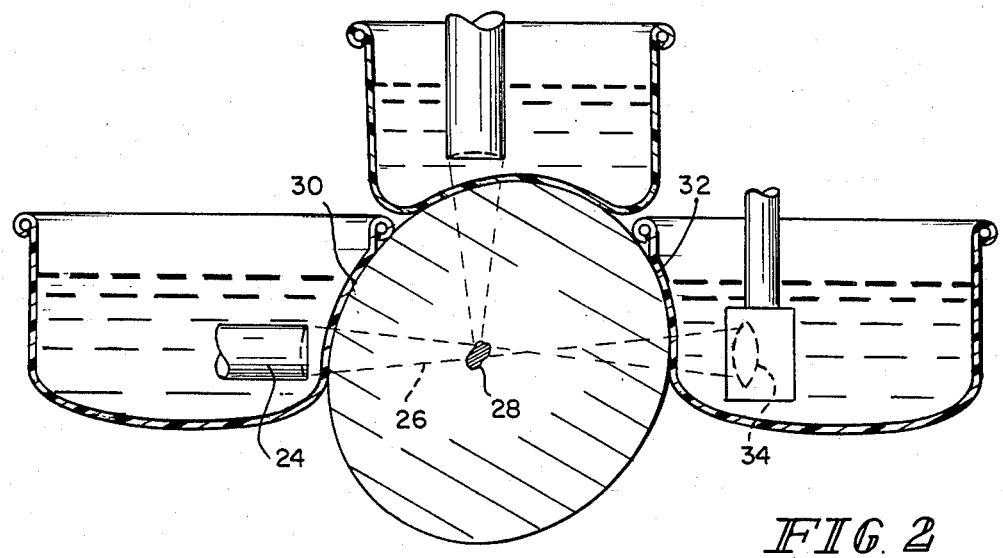
FIG. 2 is a diagrammatic illustration of an apparatus according to the present invention.

Referring to FIG. 2, a set of experiments was conducted to determine all attenuation losses due to the tissue being heated. The system of FIG. 2 has a means 24 for producing an ultrasonic beam 26 which illustratively has a SPTP of 200 W/cm$^2$ in target 28. Target 28 is illustratively a mass of tissue disposed between a skin layer 30 on one side of a body member and skin layer 32 on the opposite side of the body member. A phase insensitive thermocouple probe 34 is disposed on the side of the body member opposite the ultrasonic beam producing means 24 as a receiver. Using this setup, sample data on attenuation for the tissue of target 28 was determined, attenuation being defined as the total loss in power intensity of ultrasonic beam 26, including absorption losses, as the beam passes through the body, including target 28. Table 2 shows the change in transmitted intensity data due to the absorption coefficient change and other insertion losses.

| Thermocouple Probe Reading | Temperature |
|---|---|
| 0.94 | 37° C. |
| 1.40 | 48.6° C. |

Thus, an approximate 40% increase in the transmission of sound intensity was observed for an 11.6° C. temperature rise. Therefore, assuming a linear relationship between output temperature and output sound intensity for each 1° C. temperature rise, the transmitted sound intensity increases approximately 3.5%.

In order to control the temperature for hyperthermia treatment of human cancer, it is necessary to know the tissue temperature of the tissue being heated within ±0.5° C., preferably ±0.1° C. in both the normal, abnormal, and transition tissue regions. This objective can be accomplished with the non-invasive finite amplitude ultrasound interrogation of this invention utilizing a number of beam spatial formats.

Figure 3:
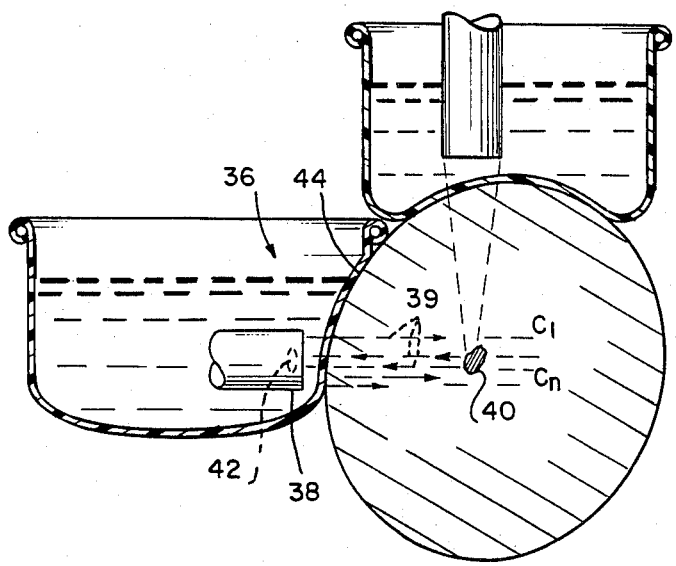
FIG. 3 is a diagrammatic illustration of an apparatus according to the present invention.

Referring to FIG. 3, a pulse-echo method of non-invasively measuring the temperature of the tissue being irradiated is shown. Non-invasive thermometry system 36 includes means 38 for producing an ultrasonic interrogation beam having a power intensity level in target 40 in the non-linear range. System 36 also includes an echo transducer 42 which is mounted substantially at the point where means 36 generates ultrasonic beam 39. Target 40, which is illustratively a tumor region, is located at some depth beneath the skin 44.

Means 36 produces a plurality, $c_1 \ldots c_n$, of ultrasonic interrogating beams 38 such that pulse-echo line-by-line data can be taken before hyperthermia induction. Illustratively, an A-mode scanner is utilized to produce the pulse-echo line-by-line data. This interrogation of target 40, $c_1$ to $c_n$, yields an attenuation profile for the normal temperature distribution. The normal temperature distribution for target 40 would be the normal body temperature. During the heating phase of the hyperthermia treatment as well as during the entire treatment period, pulse-echo data is continually acquired and an attenuation profile related to the temperature rise induced is determined based upon a priori information of attenuation loss versus temperature rise for similar tissue. Basically, for each type of tissue which undergoes hyperthermia treatment, changes in the attenuation profile related to various temperature rises are experimentally determined and stored. Then, during hyperthermia treatment, the changes in the attenuation profile as determined during treatment are compared with the experimentally determined changes in attenuation profiles and the change in temperature is determined based upon a comparison between the changes in the attenuation profiles determined during treatment and the experimentally determined changes in attenuation profiles.

Either a phase sensitive (piezoelectric crystal) pulse-echo system can be used, for a non-phase sensitive pressure receiver system can be used. Since the pulse repetition frequency of the interrogating beam typically is on the order of 1 KHz, the attenuation loss can be averaged rapidly in real time over a great number of pulses. Illustratively, 5-10 pulses can be used to generate each attenuation loss figure, although more pulses can be utilized within the real time constraints of the data processor being used, if more accuracy is desired. Illustratively, the frequency of the interrogating beam is in the 1 MHz-10 MHz range. Further gains in accuracy can be achieved by interrogating target 40 from a variety of angles.

The pulse-echo method requires a known geometric registration between the transducer beam axis and the tissue region being interrogated. However, this registration accuracy generally will not be as stringent as that required for other computer tomographic methods (X-ray computer tomography (CT) and nuclear magnetic resonance computer tomography (NMR-CT)).

Figure 4:
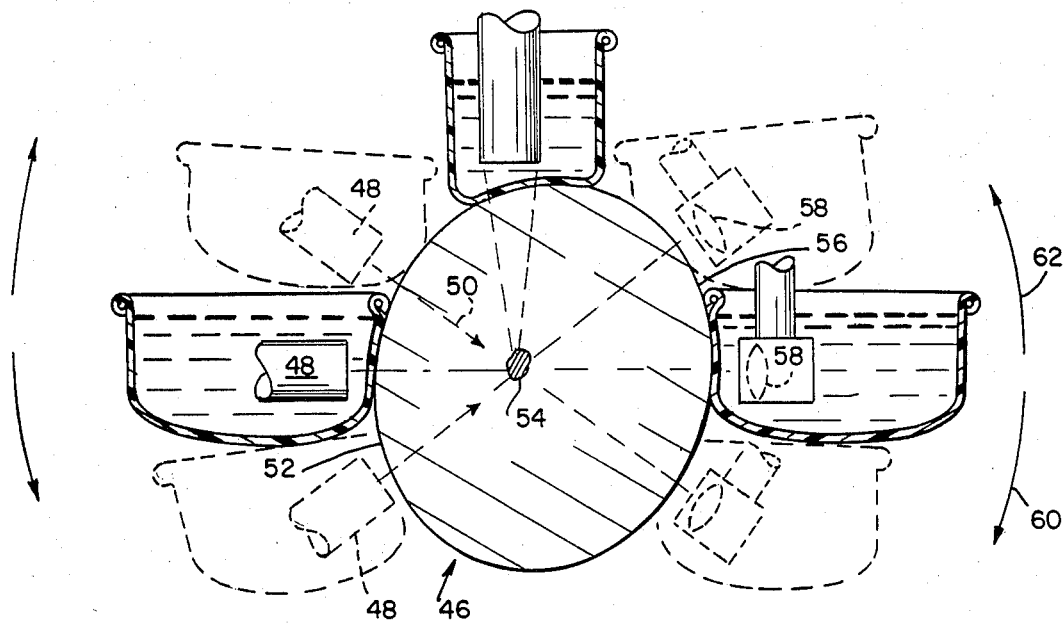
FIG. 4 is a diagrammatic illustration of an apparatus according to the present invention.

Referring to FIG. 4, a non-invasive method of measuring temperature rise in tissue undergoing temperature change utilizing pulse transmission is shown. The non-invasive thermometry system 46 includes a transducer 48 for generating ultrasonic beam 50. Ultrasonic beam 50 passes through skin 52 on one side of a body member, through target 54, which is illustratively a tumor, and through skin 56 on the other side of the body member. A receiver 58 is disposed on the side of the body member opposite the side on which transducer 48 is disposed. Illustratively, transducer 48 and receiver 58 move in the same direction, that is, either clockwise or counterclockwise around the body member as shown by arrows 60, 62, respectively. Ultrasonic beam 50 has a power intensity in the non-linear range. This method is similar to X-ray CT in that a sender and receiver are used and the attenuation profile (which is directly related to the temperature profile) is computed throughout the region interrogated.

Implementation of this temperature profiling method requires interrogation of the tissue before the temperature increase is started. This interrogation should preferrably begin at the coupler-tissue interface and progress inwardly to the desired site. This inward progression is accompanied by attenuation correction for each frequency component of the interrogating beam so that the normal base temperature attenuation for each frequency component at each tissue depth can be recorded for reference before the temperature change is initiated. Knowledge of this frequency spectrum of attenuation at each tissue depth is used to compute the delivered intensity at each tissue site and to compute the insertion loss in the tissue on the returned echo from each site. Both the forward (to a receiver) and reverse (detched echo) insertion losses as functions of frequency are needed for the final computation of temperature change at each tissue site.

Figure 5:
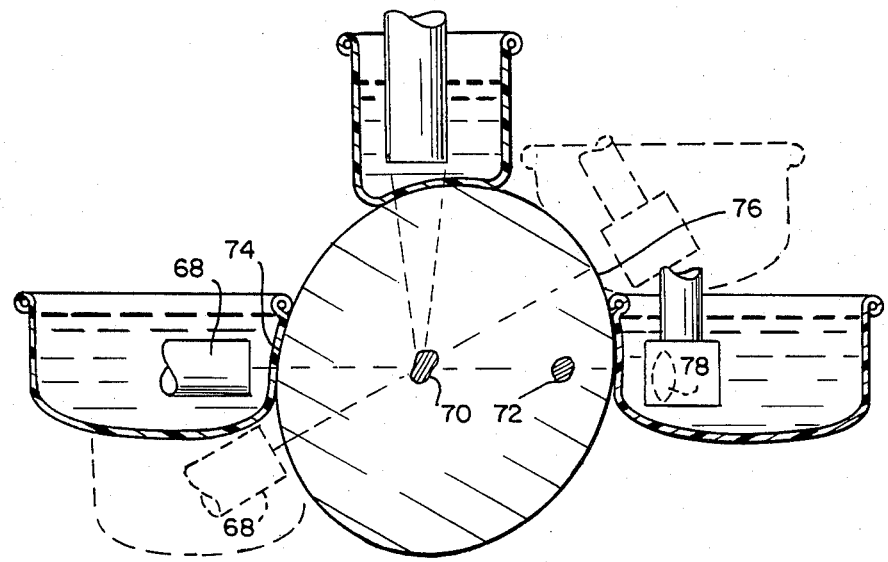
FIG. 5 is a diagrammatic illustration of an apparatus according to the present invention.

Referring to FIG. 5, this technique is particularly useful where a mass 70 of tissue is desired to be treated which lies in line with another mass 72 of tissue which is also being heated. That is, in order to determine the temperature changes at the first "hot spot," 70 it is necessary to know what is happening at the other "hot spot" 72. In FIG. 5, the source 68 of ultrasound energy and its coupler are moved relative to the localized heated regions 70, 72. By moving the source 68 and receiver 78 into the orientation illustrated in broken lines, the temperature of hot spot 70 can be isolated. The temperature information thus obtained can be used to recover the temperature of hot spot 72 as well.

The necessity and virtue of this interrogating format lies in the direct experimental determination of the base temperature values which are obtained at a high acquisition rate. Illustratively, the interrogating beam has a 1 KHz pulse repetition frequency. Once the frequency spectrum of losses is determined for the tissue region of interest, hyperthermic treatment can be initiated. Again, during hyperthermic treatment, the interrogating beam is used to interrogate the tissue region non-invasively starting at the surface.

Changes in the attenuation profile after correction for continually changing insertion losses can be interpreted in terms of a temperature change based upon a priori knowledge of tissue attenuation loss as a function of temperature for the specific spectral distribution of frequencies when the site of interrogation is subjected to finite amplitude ultrasound. Typically, the beam 50 has a power intensity level of 200 W/cm$^2$ and above in SPTP acoustic intensity in target 54.

Alternatively, a thermocouple can be invasively placed at a selected point so that one absolute internal temperature can be obtained at one point in the tissue. This absolute temperature reference is then used to provide data needed for all subsequent measurements in the tissue volume. Illustratively, a thermocouple can be placed just beneath the skin to minimize the trauma caused by the invasive placement of the thermocouple.

Although the invention has been described in detail with reference to certain preferred embodiments and specific examples, variations and modifications exist within the scope and spirit of the invention as described and as defined in the following claims.

What is claimed is:

1. In a method of non-invasively determining a temperature change in tissue, comprising the steps of irradiating the tissue with an ultrasonic beam, receiving the irradiating ultrasonic beam a first time after it has passed through the tissue and been attenuated thereby, determining the attenuation of the power intensity of the irradiating beam due to its passage through the tissue, irradiating the tissue a second time with an ultrasonic beam, receiving the irradiating ultrasonic beam a second time after it has passed through the tissue and been attenuated thereby, determining for a second time the attenuation of the power intensity of the irradiating beam due to its passage through the tissue, comparing the attenuations of the intensity of the ultrasonic beam received the first and second times due to the tissue, and determining the temperature change of the tissue based upon the comparison, the improvement wherein the irradiating ultrasonic beam is in the non-linear power range in the tissue both the first and second times.

2. The method of claim 1 wherein the irradiating ultrasonic beam power in the tissue is at least 100 watts/cm$^2$ both the first and second times.

3. The method of claim 1 wherein the step of determining the attenuation of the power intensity of the irradiating beam due to its passage through the tissue comprises the steps of measuring the power intensity of the irradiating power beam at its origin, measuring the power intensity of the irradiating beam as it is received, and comparing the power intensity of the irradiating beam at its origin to the power intensity of the irradiating beam as it is received.

4. The method of claim 1 wherein the step of determining the temperature change of the tissue based upon the comparison comprises the step of predetermining a range of attenuations for a range of temperatures for a type of tissue similar to the tissue.

5. In an apparatus for non-invasively determining a temperature change in tissue, the apparatus comprising means for irradiating the tissue a first time and a second time with an ultrasonic beam, means for receiving the irradiating ultrasonic beam a first time and a second time after it has passed through the tissue and been attenuated thereby, means for determining a first time and a second time the attenuation of the power intensity of the irradiating beam due to its passage through the tissue, means for comparing the attenuations of the intensity of the ultrasonic beam received the first and second times due to the tissue, and means for determining the temperature change of the tissue based upon the comparison, the improvement wherein the means for irradiating the tissue a first time and second time with an ultrasonic beam comprises means for irradiating the tissue a first time and a second time with an ultrasonic beam whose power intensity is in the non-linear power range in the tissue both the first and second times.

6. The apparatus of claim 5 wherein the means for irradiating the tissue a first time and a second time with an ultrasonic beam whose power intensity is in the non-linear power range in the tissue comprises means for irradiating the tissue a first time and a second time with an ultrasonic beam whose power intensity is at least 100 watts/cm$^2$ in the tissue.

7. The apparatus of claim 5 wherein the means for determining the attenuation of the power intensity of the irradiating beam due to its passage through the tissue comprises means for measuring the power intensity of the irradiating beam at its origin and for measuring the power intensity of the irradiating beam as it is received, and means for comparing the power intensity of the irradiating beam at its origin to the power intensity of the irradiating beam as it is received.

8. The apparatus of claim 5 wherein the means for determining the temperature change of the tissue based upon the comparison comprises means for storing a predetermined range of attenuations and a corresponding predetermined range of temperatures for a type of tissue similar to the tissue.

* * * * *